US008048429B2

(12) United States Patent
Sterner et al.

(10) Patent No.: US 8,048,429 B2
(45) Date of Patent: Nov. 1, 2011

(54) INACTIVATED CHIMERIC FLAVIVIRUS

(75) Inventors: Frank Jay Sterner, Rehoboth Beach, DE (US); Daniel Ghislena Emiel Goovaerts, Lichtaart (BE); Melissa Anne Lum, Rehoboth Beach, DE (US); Mark William Mellencamp, St. Joseph, MO (US)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 11/473,600

(22) Filed: Jun. 23, 2006

(65) Prior Publication Data

US 2007/0009548 A1 Jan. 11, 2007

Related U.S. Application Data

(60) Provisional application No. 60/693,629, filed on Jun. 24, 2005.

(51) Int. Cl.
*A61K 39/295* (2006.01)
*A61K 39/12* (2006.01)

(52) U.S. Cl. ....................... 424/202.1; 424/218.1; 435/5

(58) Field of Classification Search ....................... None
See application file for complete search history.

(56) References Cited

U.S. PATENT DOCUMENTS

| | | | |
|---|---|---|---|
| 6,184,024 | B1 | 2/2001 | Lai et al. |
| 6,372,221 | B2 | 4/2002 | Mannhalter et al. |
| 6,432,411 | B1 | 8/2002 | Ivy et al. |
| 6,541,011 | B2 | 4/2003 | Punnonen et al. |
| 6,676,936 | B1 | 1/2004 | Lai et al. |
| 6,682,883 | B1 | 1/2004 | Monath et al. |
| 6,696,281 | B1 | 2/2004 | Chambers et al. |
| 6,878,372 | B2 | 4/2005 | Monath et al. |
| 6,962,708 | B1 | 11/2005 | Chambers et al. |
| 2003/0022849 | A1 | 1/2003 | Chang |
| 2003/0091595 | A1 | 5/2003 | Chu |
| 2003/0104008 | A1 | 6/2003 | Loosmore et al. |
| 2004/0037848 | A1 | 2/2004 | Audonnet et al. |
| 2004/0052818 | A1 | 3/2004 | Heinz |
| 2004/0223979 | A1 | 11/2004 | Chambers et al. |
| 2004/0241191 | A1 | 12/2004 | Loosmore et al. |
| 2005/0031641 | A1 | 2/2005 | Loosmore et al. |
| 2005/0163804 | A1 | 7/2005 | Chang |
| 2005/0255127 | A1 | 11/2005 | Loosmore et al. |

FOREIGN PATENT DOCUMENTS

| | | |
|---|---|---|
| WO | WO 2006/115548 | 11/2006 |
| WO | WO 2006/116182 | 11/2006 |

OTHER PUBLICATIONS

Arroyo et al. Journal of Virology, Nov. 2004, 78(22):12497-12507.*
"Japanese Encephalitis Virus Vaccine Inactivated" 8 pages, Product Information , Aventis Pasteur Inc., Swiftwater, PA (1997).
Ashkenazi et al., Pediatr Infect Dis. J., Oct. 2006; 25(10) ; 870-9, abstract only.
Belshe et al., N. Engl, J. Med. Feb. 2007 ; 356-(7) ; 685-96, abstract only.
Chambers, Thomas J., et al. "Yellow Fever/Japanese Encephalitis Chimeric Viruses: Construction and Biological Properties" Journal of Virology, 73'4 :3095-3101 (Apr. 1999).
Monath, Thomas P. and Heinz, Franz X., Fields Virology, Chapter 31, Flaviviruses, 3rd Edition, Raven-Lippincott, New York 1996, pp. 961-1034.

* cited by examiner

*Primary Examiner* — Stacy B. Chen
(74) *Attorney, Agent, or Firm* — William M. Blackstone

(57) ABSTRACT

Embodiments of the present invention generally provide an inactivated chimeric virus vaccine and/or immunogenic composition for the treatment or prevention of viral infection. Further, various other embodiments of the present invention generally relate to methods of preventing and treating virus infection in such animals with the inactivated vaccine and/or immunogenic composition. Other embodiments comprise methods of preparing a vaccine or immunogenic composition for the treatment or prevention of viral infection in such animals.

9 Claims, No Drawings

INACTIVATED CHIMERIC FLAVIVIRUS

CROSS REFERENCE TO RELATED APPLICATIONS

This applications claims the benefit under 35 U.S.C. §119 of U.S. Provisional Application 60/693,629, filed on Jun. 24, 2005, which is hereby incorporated by reference in its entirety.

FIELD OF THE INVENTION

This invention is directed to new and improved methods of preventing and treating flavivirus and other closely related viral infection in animals.

BACKGROUND OF THE INVENTION

Flaviviruses are small, enveloped, positive-strand RNA viruses that are of concern in many medical and veterinary settings throughout the world. West Nile virus (WN, or WNV), for example, which is a member of the flavivirus family, is the causative agent of WN encephalitis, an infectious, non-contagious, arthropod-borne viral disease (In Virology, Fields (ed.), Raven-Lippincott, New York, 1996, pp. 961-1034). The virus has been found in Africa, western Asia, the Middle East, the Mediterranean region of Europe, and, recently, in the United States. Mosquitoes become infected with the virus after feeding on infected wild birds, and then transmit the virus through bites to humans, birds, and animals, such as horses, sheep, cattle, and pigs.

West Nile virus is an emerging infectious disease. West Nile virus was first isolated in Uganda in 1937. Today it is most commonly found in Africa, West Asia, Europe, and the Middle East. However, it made its first recognized appearance in the United States in 1999. By 2004, the virus had been found in birds and mosquitoes in every state except Alaska and Hawaii.

Other well-known diseases caused by flaviviruses include yellow fever, Japanese encephalitis, Dengue, and Saint Louis encephalitis. Flavivirus infections are commonly transmitted by ticks and/or mosquitoes.

The primary hosts for West Nile are only mosquitoes and birds. Other animal species, such as humans, and animals, such as horses, sheep, cattle, and pigs, and the like are thought only to be incidental hosts that become infected when an infected female mosquito bites the incidental host.

People who contract West Nile virus usually experience only mild symptoms including fever, headache, body aches, skin rash, and swollen lymph glands. If West Nile virus enters the brain, however, it can cause life-threatening encephalitis or meningitis. Life-threatening cases primarily occur in the elderly. Recent studies have shown that West Nile virus can be transmitted through blood transfusions and organ transplants. Some health experts also believe it is possible for West Nile virus to be transmitted from a mother to her unborn child, and through breast milk.

There are many development projects for West Nile virus vaccine approaches, including live chimeric vaccines (which combine genes from more than one virus into a single vaccine), naked DNA vaccines, and vaccines containing cocktails of individual West Nile proteins, and the like. However, there is no approach making use of an inactivated chimeric vaccine.

Flavivirus proteins are produced by translation of a single, long open reading frame to generate a polyprotein, which undergoes a complex series of post-translational proteolytic cleavages by a combination of host and viral proteases to generate mature viral proteins. The virus structural proteins are arranged in the polyprotein in the order C-prM-E, where "C" is capsid, "prM" is a precursor of the viral envelope-bound M (membrane) protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polypeptide.

In 2003, human clinical trials of a West Nile live, attenuated virus vaccine were begun by Acambis (Cambridge, Mass.). The Acambis live, attenuated vaccine is based on a vaccine already used for preventing yellow fever, a disease caused by a different flavivirus.

One Acambis live, attenuated vaccine contains genes from two different viruses, yellow fever and West Nile, and is an example of a chimeric virus. This Acambis live, attenuated vaccine comprises a Yellow Fever virus with a few genes replaced with genes for surface proteins of West Nile virus.

Details of making this live, attenuated chimeric Acambis vaccine are provided, for example, in U.S. Pat. Nos. 6,962,708 and 6,696,281 and Chambers et al., J. Virol. 73:3095-3101, 1999, which are each incorporated by reference herein in their entirety. Further methods of use and diagnostics for the Acambis live, attenuated chimeric vaccine are provided in U.S. Pat. Nos. 6,682,883 and 6,878,372, which are each incorporated by reference herein in their entirety.

The results of such live, attenuated vaccines have proven successful and trials continue. However, certain risks may accompany the use of a live, attenuated virus vaccine. These risks are even more pronounced for immuno-compromised subjects, the elderly subjects, pregnant subjects, and other subjects with a weakened or stressed immune system. Quite often, live, attenuated virus vaccines have been demonstrated to be either under-attenuated (cause disease) or over-attenuated (fail to immunize). It is also possible for an optimally-attenuated live virus vaccine to revert to a virulent (disease-causing) form through mutation. However, it should be noted that the YF-WN from Acambis has shown no indication of reversion to virulence. There are additional concerns with live attenuated vaccines. For example, live Dengue viruses are also sensitive to heat, making it difficult and costly to maintain the vaccine in some tropical and subtropical countries where the vaccine may be needed most. Accordingly, a vaccine is needed in the art for safely treating and/or preventing flavivirus infections, such as West Nile, in subjects with these or other similar risks. Particularly for those who are immune compromised or other subjects most at risk.

However, the state of the art is that an inactivated chimeric virus vaccine is undesirable and would not be effective. U.S. Pat. No. 6,432,411 reported that efforts to make killed flavivirus vaccines have met with limited success. Primarily the studies were limited by the inability to obtain adequate virus yields from cell culture systems. Virus yields from insect cells are generally in the range of $10^4$ to $10^5$ pfu/ml, well below the levels necessary to generate a cost-effective killed vaccine. Yields from mammalian cells including LLC-MK2 and Vero cells were higher, but the peak yields, approximately $10^8$ pfu/ml from a unique Vero cell line, are still lower than necessary to achieve a truly cost-effective vaccine product.

Accordingly, the art teaches away from the use of inactivated flaviviruses as viable vaccine candidates. Moreover, there is no teaching of an inactivated chimeric vaccine for treating or preventing any flavivirus infection.

SUMMARY OF THE INVENTION

Various embodiments of the present invention comprise a vaccine or immunogenic composition for the treatment or prevention of flavivirus infection in an animal.

The invention also provides methods for preventing or treating flavivirus infections in susceptible animals, which involve administering to the subjects inactivated chimeric flaviviruses. The invention also provides the use of inactivated chimeric flaviviruses in the preparation of medicaments for use in such methods and vaccines and/or immunogenic compositions. In one embodiment of the invention, the inactivated chimeric flaviviruses can include, for example, the capsid and non-structural proteins of a first flavivirus, and the prM and envelope proteins of a second flavivirus.

In one embodiment, the present invention is directed to an inactivated chimeric flavivirus, comprising a first flavivirus in which the nucleotide sequences encoding the pre-membrane and envelope proteins are replaced with nucleotide sequences encoding pre-membrane and envelope proteins of a second flavivirus. The first flavivirus can be yellow fever virus, including yellow fever virus derived from the 17D strain. The chimeric virus can comprise a signal sequence at the amino acid terminus of the pre-membrane protein, and the signal sequence can be that of yellow fever virus. The second flavivirus can be West Nile virus.

In another embodiment, the present invention is directed to an immunogenic composition comprising an inactivated chimeric flavivirus, comprising a first flavivirus in which the nucleotide sequences encoding the pre-membrane and envelope proteins are replaced with nucleotide sequences encoding pre-membrane and envelope proteins of a second flavivirus.

In another embodiment, the present invention is directed to a vaccine comprising an inactivated chimeric flavivirus, comprising a first flavivirus in which the nucleotide sequences encoding the pre-membrane and envelope proteins are replaced with nucleotide sequences encoding pre-membrane and envelope proteins of a second flavivirus. The vaccine can further comprise i) one or more modified live viruses; ii) one or more inactive viruses; or iii) one or more bacterial antigens. The vaccine can further comprise one or more of inactive Eastern encephalomyelitis virus, inactive Western encephalomyelitis virus, inactive Venezuelan encephalomyelitis virus, inactive equine herpes virus type 1, inactive equine herpes virus type 4, inactive equine influenza virus strain Kentucky 1993/A2, inactive equine influenza virus strain Kentucky 2002/A2, inactive equine influenza virus strain New Market/2/93/A2 and a tetanus toxoid fraction.

In another embodiment, the present invention is directed to a method of preventing or treating a flavivirus infection in an animal, the method comprising administering to the animal an inactivated chimeric flavivirus (or immunogenic composition or vaccine thereof) comprising a first flavivirus in which the nucleotide sequences encoding the pre-membrane and envelope proteins are replaced with nucleotide sequences encoding pre-membrane and envelope proteins of a second flavivirus. The first flavivirus can be yellow fever virus. The yellow fever virus can be derived from the 17D strain. The second flavivirus can be West Nile virus.

In any embodiments of the present invention, the inactivated chimeric virus can be present in a concentration ranging between $10^2$ and $10^8$ plaque-forming units (pfu). Alternatively, the chimeric flavivirus can be administered at a dose ranging between $10^6$ and $10^7$ pfu. Alternatively, the chimeric flavivirus can be administered at a dose ranging between 1-10 relative antigen dose units.

In any embodiments of the present invention, the inactivated chimeric virus can be administered by a subcutaneous, intramuscular, submucosal, mucosal, or intradermal route. In an embodiment of the present invention, the inactivated chimeric flavivirus is orally administered.

Other features and advantages of the invention will be apparent from the following description.

DETAILED DESCRIPTION

As used herein, the term "vaccine(s)" means and refers to a product, the administration of which is intended to elicit an immune response(s) that can prevent and/or lessen the severity of one or more infectious diseases. Vaccines can include one or more of the following: a live attenuated or inactivated preparation of bacteria, viruses or parasites, inactivated (killed) whole organisms, living irradiated cells, crude fractions or purified immunogens, including those derived from recombinant DNA in a host cell, conjugates formed by covalent linkage of components, synthetic antigens, polynucleotides (such as plasmid DNA vaccines), living vectored cells expressing specific heterologous immunogens, or cells pulsed with immunogen.

As used herein, "chimeric virus" refers to a virus having a genome containing sequences from two or more different viruses, including different viral strains. Unless otherwise stated, "chimera" refers to a chimeric virus. A non-limiting example of a chimeric virus is the YF/WN chimera, which is a chimeric flavivirus.

As used herein, "chimeric flavivirus" refers to a virus having a genome containing sequences from two or more different flaviviruses, including different flavivirus strains. As described above, a non-limiting example of a chimeric flavivirus is the YF/WN chimera.

As used herein, "West Nile chimeric virus", "West Nile chimera", "YF/WN virus" and "YF/WN chimera" refer to a chimeric live, attenuated virus, comprising the 17D vaccine strain of yellow fever virus (YFV) in which the nucleotide sequences encoding the pre-membrane (prM) and envelope (E) proteins are replaced by the nucleotide sequences encoding the prM and E proteins of West Nile Virus (WNV), so that the prM and E proteins of West Nile virus are expressed, and the capsid protein of the chimeric virus is from the yellow fever virus. The skilled artisan will readily appreciate that chimeric flaviviruses comprising components of yellow fever virus and West Nile virus can be made other than the specific chimeric flavivirus described in this paragraph.

West Nile chimeric virus (or, YF/WN virus) can be inactivated using techniques well known to the skilled artisan. For example, West Nile chimeric virus (or, YF/WN virus) can be inactivated with chemical inactivating agents or other physical means such as heat. Non-limiting examples of chemical inactivating agents include binary ethylenimine (BEI) or formalin (a 37% solution of formaldehyde).

Live virus can be inactivated using BEI by first mixing binary ethyleneamine (BEA) powder with a sodium hydroxide solution. After BEI is generated in the basic environment, the BEI solution is added to a solution containing live virus to give a final BEI concentration of 0.5 mM to 10 mM. This solution can then be incubated from 4-37° C. for 24-96 hours. Sodium thiosulphate can then be added after the virus is inactivated to neutralize any remaining BEI.

Live virus can also be inactivated with formalin (37% solution of formaldehyde). Here, formalin is added to a solution containing live virus to give a final formalin concentration of 0.05-2% v:v (formalin:live viral solution). This solution can then be incubated from 4-37° C. for 24-96 hours.

As used herein, the term "antigen" means and refers to a virus, a bacteria, parts of a virus or bacteria or a foreign protein that acts to stimulate the immune system in an animal. The immune system can be stimulated to cause the white blood cells to attack and destroy the antigen or to produce a protein molecule, which attaches to the antigen and either kills the antigen or makes it inactive. As used herein, the term "antibody" means and refers to a protein-containing molecule that an animal's immune system makes that reacts with an antigen to make it inactive.

As used herein, the term "animal" means and refers to both human and non-human animals.

As used herein, the term "vaccine strain" means and refers to a viral strain suitable for use in an immunogenic composition or vaccine. A "vaccine strain" can comprise, but is not necessarily limited to, a non-pathogenic strain or relatively non-pathogenic strain, a killed strain, and/or an attenuated strain.

As used herein, the term "lyophilize," and conjugations thereof, means and refers to freeze drying. As used herein, the term "animal origin" means and refers to originating from animals. Likewise, the term "non-animal origin" means and refers to not originating directly or indirectly from animals.

As used herein, the term "stabilize," and conjugations thereof, means and refers to make or hold stable, firm, steadfast and to maintain at about a given or substantially unfluctuating level, about a given or substantially unfluctuating quality and about a given or substantially unfluctuating quantity. However, it is understood that some fluctuation in the level, quality, and/or quantity of the stabilized composition may be encountered. Embodiments of the present invention are intended to encompass stabilizers that allow such fluctuations. Without limitation, stabilizers include dry stabilizers, bulk stabilizers, cryoprotectants, thermo-stabilizers, osmoprotectants, desiccation protectants, and the like. Such terms are specifically meant to be included within the stabilizers of the present invention.

As used herein, the term "protein" means and refers to a molecular chain of amino acids. A protein is not of a specific length and can, if required, be modified in vivo or in vitro, by, e.g. glycosylation, amidation, carboxylation or phosphorylation. Inter alia, peptides, oligopeptides and polypeptides are included within the definition of protein. A protein or peptide can be of biologic and/or synthetic origin.

As used herein, the term "nucleic acid" means and refers to a molecular chain of ribonucleic acids or deoxyribonucleic acids. A nucleic acid is not of a specific length, therefore polynucleotides, genes, open reading frames (ORF's), probes, primers, linkers, spacers and adaptors are included within the definition. A nucleic acid can be of biologic and/or synthetic origin. The nucleic acid may be in single stranded or double stranded form. The single strand may be in sense or anti-sense orientation. Also included within the definition are modified RNAs or DNAs. Modifications in the bases of the nucleic acid may be made, and bases such as inosine may be incorporated. Other modifications may involve, for example, modifications of the backbone.

As used herein, a pharmaceutically acceptable carrier is understood to be a compound that does not adversely affect the health of the animal or organism to be vaccinated, at least not to the extent that the adverse effect is worse than the effects seen when the animal is not vaccinated. Non-limiting examples of pharmaceutically acceptable carriers include sterile water or a sterile physiological salt solution. In a more complex form the carrier can be a buffer.

As used herein, the term "carbohydrate" means and refers to mono-, di-, oligo-, and poly-saccharides.

As used herein, the term "feline" means and refers to any animal of or pertaining to the genus *Felis*, or family Felidae, cat family, such as, but not limited to, a cat, a lion, a tiger, a mountain lion, a puma, a jaguar, a bobcat, an ocelot and the like.

As used herein, the term "canine" means and refers to any animal of or pertaining to the genus *Canis*, dog family, such as, but not limited to, a dog, wolf, and the like.

As used herein, the term "equine" means and refers to any animal of or pertaining to the genus *Equis*, or family Equidae, horse family, such as, but not limited to, a horse, mule, donkey, zebra, and the like.

The present invention generally relates to compositions for and methods of preventing and treating flavivirus infection in animals. The methods of the invention involve vaccination of animals that are at risk of developing or have flavivirus infection with an inactivated chimeric flavivirus. Other aspects of the invention are directed to methods of preparing a vaccine or immunogenic composition comprising an inactivated chimeric flavivirus for the treatment or prevention of flavivirus infection in animals.

The skilled artisan will readily appreciate, however, that there are other well characterized flaviviruses and viruses closely related to flaviviruses that can be treated or prevented using inactivated chimeric viruses described by the present invention. Hence, the invention is also directed to inactivated chimeric viruses for treating or preventing diseases or illnesses associated with or caused by viruses of the family Flaviviridae or Togaviridae. Non-limiting examples of genuses of viruses falling within these families include viruses belonging to the Flavivirus, Pestivirus, Hepacivirus or Alphavirus genuses. Non-limiting examples of viruses or diseases caused by viruses belonging to these families or genuses include encephalitis viruses, Eastern Equine Encephalitis, Western Equine Encephalitis, Venezuela Equine Encephalitis, Kunjin, Murray Valley encephalitis, Louping ill viruses, Japanese encephalitis, Dengue (serotypes 1-4), Yellow Fever, Murray Valley encephalitis, St. Louis encephalitis, Rocio encephalitis, Wesselsbron, Ilheus viruses; tick-borne flaviviruses, such as Central European encephalitis, Siberian encephalitis, Russian Spring-Summer encephalitis, Kyasanur Forest Disease, Omsk Hemorrhagic fever, Powassan, Negishi, Absettarov, Hansalova, Apoi, and Hypr viruses; as well as viruses from the Hepacivirus genus (e.g., Hepatitis C virus). Additional viruses that can be treated or prevented using inactivated chimeric viruses of the present invention include those belonging to the *Pestivirus* genus (e.g., Bovine diarrhea virus), and other viruses, such as Lassa, Ebola, and Marburg viruses or other RNA viruses with a genomic construction that would be compatible with incorporation into the chimera.

Infection by any of the above described viruses (or diseases caused thereby) can be prevented or treated with the inactivated chimeric viruses described herein. In particular, with inactivated chimeric viruses that comprise a first virus in which one or more structural protein (or proteins) of the first virus has been replaced with a corresponding structural protein (or proteins) of a second virus against which protection or treatment is sought.

A preferred aspect of the invention is directed to inactivated chimeric flaviviruses, methods of making inactivated chimeric flaviviruses, vaccines comprising inactivated chimeric flaviviruses, and methods of using such vaccines. This aspect of the invention is directed to inactivated chimeric flaviviruses that comprise a flavivirus in which one or more structural proteins of a first flavivirus have been replaced with one or more corresponding structural proteins of a second flavivirus, to which immunity is sought. In one embodiment of the present invention, the chimeras consist of the backbone of a first flavivirus in which the prM and E proteins have been replaced with the prM and E proteins of a second flavivirus.

The inactivated chimeric viruses that are used in the invention can consist of any combination of viruses, provided that, as is mentioned above, the virus to which immunity is desired is the source of the inserted structural protein(s). For example, to vaccinate an animal, such as a horse, against West Nile virus infection, a chimeric flavivirus consisting of a flavivirus backbone, such as that of yellow fever (YF) virus, into which West Nile virus structural proteins, such as prM and E proteins, are inserted can be used. In this chimera, the YF prM and E proteins are replaced with those of WN. Similarly, if immunity against Japanese encephalitis (JE) virus is desired, then the prM and E proteins of JE virus can be inserted into a backbone flavivirus, such as a yellow fever virus, in place of the corresponding backbone proteins. Other flaviviruses that cause disease in horses, and for which chimeric viruses can be used for inducing protection, include Kunjin, Murray Valley encephalitis, and Louping ill viruses. In all embodiments of the present invention, the chimeric virus is then inactivated. Examples of animals that can be vaccinated and/or treated with the inactivated chimeric viruses of the present invention comprise humans, horses, pigs, sheep, cattle, domestic animals, such as cats and dogs, and domestic birds. However, in general any animal susceptible to infection from the flavivirus for which protection is sought may be vaccinated.

Thus, non-limiting examples of flaviviruses that can be used in the invention, as sources of backbone virus or structural protein inserts, include mosquito-borne flaviviruses, such as Japanese encephalitis, Dengue (serotypes 1-4), Yellow Fever, Murray Valley encephalitis, St. Louis encephalitis, West Nile, Kunjin, Rocio encephalitis, Wesselsbron, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the *Hepacivirus* genus (e.g., Hepatitis C virus). Additional viruses that can be used as the source of inserted structural proteins include viruses from the *Pestivirus* genus (e.g., Bovine diarrhea virus), and other viruses, such as Lassa, Ebola, and Marburg viruses.

In general, as is disclosed in U.S. Pat. Nos. 6,962,708 and 6,696,281, in an embodiment for the prevention or treatment of West Nile flavivirus infection, such methods entail replacing genes encoding two structural proteins [prM and E] of yellow fever 17D vaccine virus with the corresponding genes of West Nile virus and inactivating the chimeric virus. The resulting inactivated virion has the envelope of West Nile, containing structures involved in virus-cell attachment and virus internalization, all antigenic determinants for neutralization, and epitope(s) for cytotoxic T lymphocytes. The nucleocapsid (C) protein, nonstructural proteins, and non-translated termini responsible for virus replication remain those of the original yellow fever 17D virus.

One preferred embodiment of the present invention is directed to an inactivated chimeric vaccine and/or immunogenic composition for the treatment or prevention of West Nile infection, in an animal susceptible to West Nile infection. Details of making chimeric viruses including a WN/YF chimeric virus that can then be inactivated and used in various embodiments of the invention are provided, for example, in U.S. Pat. Nos. 6,962,708 and 6,696,281 and Chambers et al., J. Virol. 73:3095-3101, 1999, which are all hereby incorporated by reference in their entirety. U.S. Pat. Nos. 6,962,708 and 6,696,281 are limited, however, to live attenuated chimeric viruses, vaccines and related methods of use. There is no teaching or suggestion of using an inactivated chimeric virus, use of an inactivated chimeric virus in a vaccine, or use of an inactivated chimeric virus in any related method. In contrast to these patents, all embodiments of the present invention are directed to inactivated chimeric viruses.

Vaccine and immunogenic compositions according to the various embodiments of the present invention can be prepared and/or marketed in the form of a liquid, frozen suspension or in a lyophilized form. Typically, vaccines and/or immunogenic compositions prepared according to the present invention contain a pharmaceutically acceptable carrier or diluent customarily used for such compositions. Carriers include, but are not limited to, stabilizers, preservatives and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate or glucose), proteins (such as dried milk serum, albumin or casein) or degradation products thereof. Non-limiting examples of suitable buffers include alkali metal phosphates. Suitable preservatives are thimerosal, merthiolate and gentamicin. Diluents include water, aqueous buffer (such as buffered saline), alcohols and polyols (such as glycerol).

If desired, the inactivated vaccines according to the invention may contain an adjuvant. Suitable compounds or compositions for this purpose include HAVLOGEN® (an acrylic acid polymer-based adjuvant, Intervet Inc., Millsboro, Del.), polyacrylic acids, aluminium hydroxide, -phosphate or -oxide, oil-in-water or water-in-oil emulsion based on, for example a mineral oil, such as BAYOL™ or MARCOL™ (Esso Imperial Oil Limited, Canada), or a vegetable oil such as vitamin E acetate, and saponins. However, components with adjuvant activity are widely known and, generally, any adjuvant may be utilized that does not adversely interfere with the efficacy or safety of the vaccine and/or immunogenic composition.

Generally, the vaccine may be administered subcutaneously, intradermally, submucosally, or intramuscularly in an effective amount to prevent infection from the flavivirus of interest and/or treat an infection from the flavivirus. An effective amount is defined as an amount of immunizing inactivated chimeric material that will induce immunity in the vaccinated animals, against challenge by a virulent virus. In various other embodiments, an effective amount will induce immunity in the vaccinated animals or their progeny, against challenge by a virulent virus. Immunity is defined herein as the induction of a significant higher level of protection in a population of the animal after vaccination compared to an unvaccinated group.

Further, in various formulations of the inactivated vaccines and/or immunogenic compositions of the present invention, suitable excipients, stabilizers and the like may be added.

The inactivated chimeric virus can be formulated as a sterile aqueous solution containing between $10^2$ and $10^{12}$ infectious units (as determined prior to inactivation). In one embodiment, the inactivated chimeric virus can be formulated as a sterile aqueous solution containing between $10^7$ and $10^{10}$ infectious units (as determined prior to inactivation). Infectious units include plaque-forming units (pfu) or tissue culture infectious doses (tcid). Alternatively, the inactivated chimeric virus can be formulated as a sterile aqueous solution containing between 1-10 relative antigen dose units. The formulated inactivated chimeric virus can be provided in a dose volume of 0.1 to 1.0 ml, to be administered by, for example, subcutaneous, intramuscular, submucosal or intradermal routes. Further embodiments may be administered by a mucosal route, such as an oral route. Selection of an appropriate amount of chimera to administer can be determined by those of skill in this art, and this amount can vary due to numerous factors, including without limitation the size, type, and general health of the animal to which the chimera is to be administered.

For a greater understanding of the invention, reference should be made to the following examples and claims.

Example 1

Experimental Design:
Animals:

Six (6) yearling horses of mixed breed, both male and female, and seronegative to West Nile virus (WNV) were vaccinated with a combination vaccine containing the inactivated viral components of PRESTIGE® V+VEE vaccine (available from Intervet Inc, Millsboro, Del.) and inactivated Yellow Fever-West Nile (YF-WN) chimera, all combined with a polyacrylic acid adjuvant. PRESTIGE® V+VEE vaccine contains inactivated Eastern Encephalomyelitis virus, inactivated Western Encephalomyelitis virus, inactivated Venezuelan Encephalomyelitis virus, inactivated Equine Herpes virus types 1 and 4 (Rhinopneumonitis), inactivated Influenza virus (Kentucky strain 1993, Kentucky strain 2002, and New Market-2-93), and tetanus toxoid fractions.

The YF-WN live attenuated chimera was obtained from Acambis in Cambridge, Mass., and inactivated with binary ethyleneimine (BEI). Inactivation was accomplished by first mixing binary ethyleneamine (BEA) powder with a sodium hydroxide solution. Upon mixing, the BEA converts to BEI. This BEI liquid solution is added to a solution of live chimeric virus to give a final BEI concentration of 2 mM. The BEI/chimera solution was incubated at about 18-25° C. for about 3 days.

Another six (6) yearling horses of mixed breed, both male and female, and seronegative to West Nile virus (WNV) were vaccinated with a combination vaccine containing the inactivated viral components of PRESTIGE® V+VEE vaccine (available from Intervet Inc, Millsboro, Del.) and formalin-inactivated Yellow Fever-West Nile (YF-WN) chimera.

The YF-WN live attenuated chimera was obtained from Acambis in Cambridge, Mass., and inactivated with formalin (37% solution of formaldehyde). Inactivation was accomplished by mixing formalin solution to a solution of live chimeric virus to give a final formalin concentration of 0.1% v:v with respect to the solution of live chimeric virus. The formalin/chimera solution was incubated at about 18-25° C. for about 3 days.

Another six (6) yearling horses of mixed breed, both male and female, and seronegative to West Nile virus (WNV) were not vaccinated and used as controls.

Vaccination:

Horses received 2×1 mL dose of vaccine, intramuscular, administered 3-4 weeks apart.

Challenge Virus:

West Nile Virus (WNV), 5 $\log_{10}$ PFU/1 ml dose, administered per horse by the intrathecal route at 4 weeks post second vaccination.

Results:

| Vaccine | No. horses/ group | Results post challenge with WNV: | | | |
|---|---|---|---|---|---|
| | | ≧102.5° F. | Clin. Signs | Viremia | Histo. |
| BEI inac. YF/WN virus | 6 | 0/6 | 0/6 | 0/6 | 0/6 |
| Formalin inac. YF/WN virus | 6 | 0/6 | 0/6 | 0/6 | 1/6 |
| Unvaccinated controls | 6 | 4/6 | 5/6 | 5/6 | 5/6 |

The serological results from Example #1 follow:

Virus Neutralizing (VN) Antibody Titers to WNV in Horses Vaccinated with Two Dose of Inactivated YF-WN or One Dose of live YF-WN Chimera (from Acambis, Cambridge, Mass.)

| | VN titers (50% plaque reduction) on days post vaccination and challenge[a] | | | | | |
|---|---|---|---|---|---|---|
| | Post Vaccination | | | Post Challenge (days) | | |
| Vaccine[b] | PreVac | Post 1st | Post 2nd | 7 | 14 | 21 |
| BEI-inac | Negative | 80 | 80 | 160 | >1280 | 1280 |
| YF-WN | Negative | 40 | 40 | 80 | 640 | 640 |
| virus | Negative | 5 | 20 | 80 | >1280 | >2560 |
| | Negative | 5 | 5 | 5 | 1280 | 1280 |
| | Negative | 5 | 80 | 160 | 10240 | 2560 |
| | Negative | 5 | 5 | 320 | 5120 | 2560 |
| Formalin | Negative | 160 | 160 | 640 | >1280 | 1280 |
| Inac | Negative | 160 | 160 | >1280 | 640 | 1280 |
| YF-WN | Negative | 160 | 160 | 320 | >1280 | 1280 |
| virus | Negative | Neg | 40 | 320 | 5120 | 2560 |
| | Negative | 5 | 20 | 20 | 640 | 320 |
| | Negative | 40 | 40 | 320 | 2560 | 2560 |
| Live | Negative | 160 | N/A | 320 | >1208 | 1280 |
| YF-WN | Negative | 160 | N/A | 80 | >1280 | 640 |
| virus | Negative | 160 | N/A | 80 | >1280 | 320 |
| | Negative | 40 | N/A | 1280 | 5120 | 2560 |
| | Negative | 5 | N/A | 80 | 5120 | 2560 |
| | Negative | 640 | N/A | 1280 | 20480 | 5120 |
| Control | Negative | Negative | Negative | 320 | Dead | Dead |
| | Negative | Negative | Negative | 80 | >1280 | >2560 |
| | Negative | Negative | Negative | 5 | 640 | 640 |
| | Negative | Negative | Negative | 320 | 2560 | 1280 |

-continued

| | VN titers (50% plaque reduction) on days post vaccination and challenge[a] | | | | | |
|---|---|---|---|---|---|---|
| | Post Vaccination | | | Post Challenge (days) | | |
| Vaccine[b] | PreVac | Post 1$^{st}$ | Post 2$^{nd}$ | 7 | 14 | 21 |
| | Negative | Negative | Negative | 320 | Dead | Dead |
| | Negative | Negative | Negative | 320 | Dead | Dead |

[a]Titer values are the number-fold dilution representing the greatest dilution of serum at which 50% plaque reduction is observed relative to control. "Negative" indicates no plaque reduction observed; "80" represents an 80-fold dilution; "160" represents a 160-fold dilution, etc.; "N/A" is indicated where no second vaccination was administered; "Dead" refers to the horses.
[b]BEI or formalin inactivated YF-WN chimera was in combination with PRESTIGE ® V + VEE vaccine.

Results:

The serological results from Example #1 illustrate the unexpected results of the inactivated West Nile chimera vaccine of the present invention. It is known that live viruses, such as Acambis' live attenuated YF-WN chimera, produce both cell mediated responses and humoral responses (antibody response). However, it is generally regarded that inactivated viruses only produce humoral responses. Here, the inactivated YF-WN produces a high humoral response, as is evident from the serological data. Accordingly, and unexpectedly, the inactivated YF-WN performs as well as the live YF-WN at eliciting a humoral response. In addition to the above described advantages of using an inactivated vaccine rather than a live vaccine, the advantages of the inactivated vaccines of the present invention are unexpected.

Example 2

Experimental Design:
Animals: Horses

Six (6) yearling horses of mixed breed, both male and female, and seronegative to West Nile virus (WNV) were vaccinated with a combination vaccine containing the inactivated viral components of PRESTIGE® V+VEE vaccine (available from Intervet Inc, Millsboro, Del.) and inactivated Yellow Fever-West Nile (YF-WN) chimera. The vaccine also contained a polyacrylic acid adjuvant. PRESTIGE® V+VEE vaccine contains inactivated Eastern Encephalomyelitis virus, inactivated Western Encephalomyelitis virus, inactivated Venezuelan Encephalomyelitis virus, inactivated Equine Herpes virus types 1 and 4 (Rhinopneumonitis), inactivated Influenza virus (Kentucky strain 1993, Kentucky strain 2002, and New Market-2-93), and tetanus toxoid fractions.

The YF-WN live attenuated chimera was obtained from Acambis in Cambridge, Mass. The chimeric virus was inactivated with BEI and added to the PRESTIGE® V+VEE vaccine as described above in Example 1.

Another six (6) yearling horses of mixed breed, both male and female, and seronegative to West Nile virus (WNV) were not vaccinated and used as controls.

Vaccination

Horses received 2×1 mL dose of vaccine, intramuscular, administered 3-4 weeks apart.

Challenge Virus

Horses were challenge by placing 8-17 mosquitoes infected with WNV on each horse and allowing the mosquitoes to feed for 10-15 minutes.

Results:

| | No. | Results post challenge with WNV: | | | |
|---|---|---|---|---|---|
| Vaccine | horses/ group | ≧102.5° F. | Clin. Signs | Viremia | Histo. |
| Inac. YF/WN | 6 | 0/6 | 0/6 | 0/6 | 0/6 |
| Unvaccinated controls | 6 | 0/6 | 0/6 | 5/6 | 1/6 |

Example 3

I. Experimental Overview

The purpose of this experiment was to establish the immunogenicity of the inactivated West Nile chimeric virus contained in a combination vaccine comprising the antigenic components of PRESTIGE® V+VEE vaccine (available from Intervet Inc, Millsboro, Del.; i.e., inactivated Eastern Encephalomyelitis virus, inactivated Western Encephalomyelitis virus, inactivated Venezuelan Encephalomyelitis virus, inactivated Equine Herpes virus types 1 and 4 (Rhinopneumonitis), inactivated Influenza virus (Kentucky strain 1993, Kentucky strain 2002, and New Market-2-93 strain), and Tetanus toxoid), all combined with a polyacrylic acid adjuvant.

In particular, one purpose of this experiment was to establish the noninterference of the other vaccine fractions with the inactivated West Nile chimeric virus.

Twenty (20) male and female horses were vaccinated two times by the intramuscular (IM) route three to four weeks apart with a 1.0 ml dose of a combination vaccine comprising inactivated West Nile chimeric virus, inactivated Eastern Encephalomyelitis virus, inactivated Western Encephalomyelitis virus, inactivated Venezuelan Encephalomyelitis virus, inactivated Equine Herpes virus types 1 and 4 (Rhinopneumonitis), inactivated Influenza virus (Kentucky strain 93, Kentucky strain 2002, and New Market-2-93 strain), and Tetanus toxoid, all combined with a polyacrylic acid adjuvant. Ten additional horses served as unvaccinated controls. At 21 days post-2$^{nd}$ vaccination, vaccinated and unvaccinated control horses were challenged by the intrathecal (IT) route with virulent WNV. Two separate groups of 10 vaccinate and 5 control horses were sequentially vaccinated and challenged. Blood samples for serological evaluation were collected before vaccination, after vaccination and after challenge and tested for virus neutralization (VN) antibody titers to WNV. Blood samples were collected post-challenge for isolation of WNV. Neural tissues were collected at the time of necropsy for histological examination.

Challenge of horses with virulent WNV by the IT route resulted in signs of neurological disease that are consistent with those observed in horses infected under natural field conditions. Post-challenge, vaccinated horses showed a statistically significant reduction in clinical signs of neurological disease caused by WNV compared to unvaccinated controls and a statistically significant reduction in virus shedding between vaccinates and controls. These results established the noninterference of the other vaccine fractions on the Killed Flavivirus Chimera fraction. Additional data established the noninterference of the Killed Flavivirus Chimera fraction on the other vaccine fractions.

II. Materials and Methods

A. Animals

Thirty (30) horses of mixed sex and breed and six to nine months of age were used. Horses were identified by a freeze brand. Only horses with virus neutralizing (VN) antibody titers of $\leq 5$ to WNV as determined by a 50% plaque reduction neutralization test were used. Vaccinate and control horses were housed together in insect and rodent proof facilities during the vaccination period and moved to another facility for challenge with virulent WNV.

B. Vaccines

The vaccine contained YF/WN chimera in combination with Eastern encephalomyelitis (EE) virus, Western encephalomyelitis (WE) virus, Venezuelan encephalomyelitis (VE) virus, equine herpes virus type 1 (EHV-1), equine herpes virus type 4 (EHV-4), equine influenza virus (EIV) strain Kentucky 1993/A2, EIV strain Kentucky 2002/A2, and EIV strain New Market/2/93/A2, and tetanus toxoid fractions. The vaccine contained a polyacrylic acid adjuvant.

Two vaccines were used to demonstrate non-interference. One vaccine contained a minimum immunizing dose of inactivated YF/WN chimera and a standard release dose of the remaining inactivated viruses or tetanus toxoid fractions. The other vaccine contained a standard release dose of inactivated YF/WN chimera and a minimum immunizing dose of the remaining inactivated viruses or tetanus toxoid fractions. In each case, the component(s) present at the standard release dose did not interfere with the component(s) present at the minimum immunizing dose level.

C. Vaccination

Horses were 6 to 9 months of age at the time of the first vaccination. Horses were randomized into groups by use of a random number generator and acclimatized for a minimum of seven days. Twenty horses were vaccinated IM in the neck with two 1 ml doses of the vaccine at three weeks apart. Ten horses were used as unvaccinated controls. Two groups of horses (each containing 10 vaccinates and 5 controls) were sequentially vaccinated.

D. Blinding

Project personnel who observed clinical signs and performed laboratory testing on clinical samples were unaware to which group the horses belonged.

F. Observations and Collection of Samples Post-Vaccination

Rectal body temperatures were taken and injection site reactions were observed on days −1 through 10 post-vaccination. Body temperatures of $\geq 102.5°$ F. are considered to be an elevated temperature. Injection site reactions were scored according to a scoring method. Any systemic reactions or observations of abnormal health were recorded. Blood for serum was collected on days 0, 7, and 21 day post-first vaccination and at 21 days post-second vaccination. Neutralization antibody titers to WNV in serum samples from horses were determined by the use of a 50% plaque reduction neutralization test.

G. Challenge of Horses with Virulent WNV

At 21 days post-second vaccination, horses were challenged by IT administration of 1 ml containing virulent WNV strain NY99. Results of five replicate titrations of the challenge material were 5.0, 5.1, 5.1, 5.0, and 5.0 for a mean of 5.0 and 5.1, 5.1, 5.0, 5.0, and 5.1 for a mean of 5.1 $\log_{10}$ PFU/ml dose, for challenge groups 1 and 2, respectively. Rectal body temperatures were recorded on days −1 through 21 post-challenge. Challenge of unvaccinated control horses with WNV by the IT route resulted in clinical signs of disease that are observed in horses naturally infected with WNV under field conditions. Horses were observed during the 21 day post-challenge period for clinical signs of neurological disease, in the following categories: Changes in mentation, paresis, fasciculations, and ataxia/recumbency. For each category, clinical signs were scored as 0=none, 1=very mild and could go unnoticed, 2=moderate and 3=severe.

Upon confirmation of severe clinical disease, attempts were made to euthanize the animal within 24 hours. Horses were euthanized for humane reasons due to persistent signs of West Nile disease, or sudden acute signs coupled with recumbency and/or the inability to locomote without assistance as per Center for Veterinary Biologics Notice No. 04-09, dated Apr. 1, 2004. Any other abnormal health observations were recorded. Blood samples for serology were taken at the time of challenge and at 7, 14, and 21 days post-challenge. Blood samples for virus isolation were taken on days −1 through 10 post-challenge. Blood for serology, virus isolation, and tissues for histopathology were taken at the time of necropsy. Histopathological lesions in neural tissues were scored as 0=none, 1=very mild/mild, 2=moderate, and 3=severe.

III. Results

A. Animals and Vaccination

Body temperatures of $\geq 102.5°$ F. were recorded for one day post-first vaccination for three vaccinate horses and for two days for one control horse. Body temperatures of $\geq 102.5°$ F. were not recorded for any vaccinate or control horse after the second vaccination. All horses were in good general health at the start of the study. Vaccination site reactions were evaluated according to a scoring method (0 (no reaction) to 5 (systemic reaction)). Post-first vaccination, mild injection site reactions, of scores of 2 or less, were recorded on one or two days for three horses. Another vaccinate horse had a mild reaction that persisted through 10 days post-first vaccination but did not cause any pain or result in reluctance to move. Mild injection site reactions, of scores of 2 or less, were also observed post-second vaccination that persisted for 1 to 6 days post-vaccination. None of the injection site reactions post-first or second vaccination were noted as painful. No systemic reactions were observed in any of the horses post-first or second vaccination.

B. Serology Post-Vaccination and Post-Challenge with WNV

Serological data for vaccinated and control horses is summarized in the following tables.

Vaccinate Group: Plaque Reduction Neutralization Antibody Titers 50% (PRNT50%) to WNV Post-1$^{st}$ and 2$^{nd}$ Vaccination and Post-Challenge.

PRNT50% titers to WNV on days post-vaccination and challenge[a]:

| Horse No. | Post-Vaccination | | | | Post-Challenge | | |
|---|---|---|---|---|---|---|---|
| | Day 0 | Day 7 | Day 21[a] | Day 42[b] | Day 7 | Day 14 | Day 21 |
| 201 | Neg. | Neg. | Neg. | Neg. | ≧1280 | ≧1280 | ≧1280 |
| 205 | Neg. | Neg. | Neg. | 40 | 640 | ≧1280 | ≧1280 |
| 209 | Neg. | Neg. | Neg. | 5 | 5 | NS | NS |
| 211 | Neg. | Neg. | Neg. | 5 | 80 | ≧1280 | ≧1280 |
| 212 | Neg. | Neg. | Neg. | 10 | 640 | ≧1280 | ≧1280 |
| 214 | Neg. | Neg. | Neg. | 20 | 640 | ≧1280 | ≧1280 |
| 217 | Neg. | Neg. | Neg. | 10 | ≧1280 | ≧1280 | ≧1280 |
| 218 | Neg. | Neg. | Neg. | 20 | ≧1280 | ≧1280 | ≧1280 |
| 220 | Neg. | Neg. | Neg. | Neg. | 20 | ≧1280 | ≧1280 |
| 223 | Neg. | Neg. | Neg. | Neg. | 320 | ≧1280 | ≧1280 |
| 227 | Neg. | Neg. | Neg. | Neg. | 640 | ≧1280 | ≧1280 |
| 229 | Neg. | Neg. | Neg. | Neg. | 20 | ≧1280 | ≧1280 |
| 230 | Neg. | Neg. | Neg. | 5 | 160 | ≧1280 | ≧1280 |
| 232 | Neg. | Neg. | Neg. | 20 | 10 | ≧1280 | ≧1280 |
| 233 | Neg. | Neg. | 20 | 20 | 20 | ≧1280 | ≧1280 |
| 234 | Neg. | Neg. | Neg. | 10 | 20 | ≧1280 | ≧1280 |
| 235 | Neg. | Neg. | Neg. | 5 | 80 | ≧1280 | ≧1280 |
| 238 | Neg. | Neg. | Neg. | 10 | 40 | ≧1280 | ≧1280 |
| 248 | Neg. | Neg. | Neg. | 160 | 160 | ≧1280 | ≧1280 |
| 254 | Neg. | Neg. | Neg. | Neg. | 320 | ≧1280 | ≧1280 |

[a]Titer values are the number-fold dilution representing the greatest dilution of serum at which 50% plaque reduction is observed relative to control.
[b]= Day 21 is day of 2nd vaccination,
[c]= Day 42 is 21 days post-2nd vaccination and day of challenge
Neg. = Negative,
NS = No sample, euthanized Control Group: Plaque Reduction Neutralization Antibody Titers 50% (PRNT50%) to WNV Post-1st and 2nd Vaccination and Post-Challenge.

PRNT50% titers to WNV on days post-vaccination and challenge[a]:

| Horse No. | Post-Vaccination | | | | Post-Challenge | | |
|---|---|---|---|---|---|---|---|
| | Day 0 | Day 7 | Day 21[b] | Day 42[c] | Day 7 | Day 14 | Day 21 |
| 202 | Neg. | Neg. | Neg. | Neg. | ≧1280 | NS | NS |
| 204 | Neg. | Neg. | Neg. | Neg. | 640 | ≧1280 | ≧1280 |
| 206 | Neg. | Neg. | Neg. | Neg. | 40 | NS | NS |
| 208 | Neg. | Neg. | Neg. | Neg. | 20 | 640 | ≧1280 |
| 216 | Neg. | Neg. | Neg. | Neg. | 20 | ≧1280 | ≧1280 |
| 219 | Neg. | Neg. | Neg. | Neg. | ≧1280 | NS | NS |
| 221 | Neg. | Neg. | Neg. | Neg. | 320 | NS | NS |
| 225 | Neg. | Neg. | Neg. | Neg. | 40 | ≧1280 | ≧1280 |
| 231 | Neg. | Neg. | Neg. | Neg. | 40 | ≧1280 | ≧1280 |
| 239 | Neg. | Neg. | Neg. | Neg. | ≧1280 | ≧1280 | ≧1280 |

[a]Titer values are the number-fold dilution representing the greatest dilution of serum at which 50% plaque reduction is observed relative to control.
[b]= Day 21 is day of 2nd vaccination,
[c]= Day 42 is 21 days post-2nd vaccination and day of challenge
Neg. = Negative,
NS = No sample, euthanized All vaccinate and control horses were seronegative to WNV at the time of vaccination and at 7 days post-first vaccination. The lack of an anamnestic response to WNV in vaccinates post-first vaccination indicated no previous exposure to WNV. Plaque reduction virus neutralizing antibody titers to WNV were detected in one vaccinate post-first vaccination and were detected in 14 of 20 vaccinates at 21 days post-second vaccination. All unvaccinated control horses remained seronegative throughout the first and second vaccination period. These results demonstrate that the control horses were not exposed to WNV during the vaccination period, which establishes the validity of the study. High levels of virus neutralizing antibody to WNV were detected in both vaccinate and control horses post-challenge.

C. Rectal Body Temperatures and Neurological Signs in Horses Post-Challenge with Virulent WNV Individual body temperatures of horses post-challenge were observed. Six of the 20 vaccinate horses exhibited body temperatures of ≧102.5° F. for one or two individual days post-challenge and three of these six vaccinates exhibited body temperatures of ≧102.5° F. for two or more consecutive days. Seven of 10 unvaccinated control horses exhibited body temperatures of ≧102.5° F. on any day post-challenge and all seven of these controls exhibited body temperatures of ≧102.5° F. for two or mores consecutive days. Post-challenge temperatures were compared by a repeated measures analysis of variance using a model that included the effects of treatment, days, and the interaction of treatment and days. There was a significant difference (P<0.05) in body temperatures between vaccinates and control horses on days 8 through 10 post-challenge. Four of the 10 controls were euthanized by day 10 post-challenge due to the severity of clinical signs of disease.

Challenge of unvaccinated control horses with WNV by the intrathecal (IT) route resulted in clinical signs of disease that are consistent with those observed in horses naturally infected with WNV under field conditions. Clinical signs that included changes in mentation, paresis, fasciculations, and ataxia/recumbency were also observed. Post-challenge, 7 of 10 (70%) unvaccinated control horses demonstrated moderate or severe signs of WNV neurological disease for two or more consecutive days or demonstrated a severe overall health condition due to WNV infection such that euthanasia was warranted for humane reasons. Horses were euthanized for humane reasons due to persistent signs of West Nile disease, or sudden acute signs coupled with recumbency and/or the inability to locomote without assistance.

The case definition of infection with WNV and primary outcome for demonstration of disease caused by WNV was defined as horses having moderate or severe signs of disease for two or more consecutive days in any of the categories of: Changes in mentation, paresis, fasciculations, and ataxia/recumbency or any animal in which euthanasia was required due to overall severe health condition of the animal as a result of WNV infection. These criteria had to be satisfied in order for the primary outcome to be a failure; otherwise, the horse was considered a success.

Only 5 of 20 (25%) of the vaccinated horses demonstrated moderate or severe signs of WNV neurological disease for two consecutive days post-challenge or were euthanized compared to 7 of 10 (70%) of the controls. Analysis for the primary outcome was performed in SAS with the FREQ Procedure. Analysis of the proportion of horses meeting the case definition showed there was a significant (P<0.02) difference between vaccinates and controls. The odds ratio indicated that vaccinated horses were 6 times more likely to be protected against neurological signs of WNV disease. A statistically (P<0.05) higher proportion of controls were euthanized due to signs of WNV disease compare to controls.

D. Virus Isolation from Serum Post Challenge with Virulent WNV

Results of WNV isolated from serum of horses post challenge were also observed. WNV was recovered from the serum from 6 of 20 vaccinate and from 10 of 10 control horses on days 1 through 4 post-challenge. Significantly (P<0.05) more controls were viremic compared to vaccinates and controls were significantly (P<0.01) viremic more days compared to vaccinates.

E. Histopathology of Neural Tissues in Vaccinates and Controls Post-Challenge with Virulent WNV At the time of necropsy, neural tissue from the pons, medulla, and hypothalamus/thalamus were collected and analyzed for histopathology due to viral encephalitis. In general, there was reduced histopathology in vaccinates compared to controls but there was not a statistically significant difference.

IV. Conclusion

Challenge of horses with virulent WNV by the IT route resulted in signs of neurological disease that are consistent with those observed in horses infected under natural field conditions and are consistent with neurological disease observed in studies with a monovalent vaccine to WNV. Post-challenge, vaccinated horses showed a statistically significant reduction in clinical signs of neurological disease caused by WNV compared to unvaccinated controls and a statistically significant reduction in virus shedding between vaccinates and controls. These results meet the criteria for satisfactory demonstration of the immunogenicity of the West Nile Virus, Killed Flavivirus Chimera fraction contained in a combination vaccine comprising the components of PRESTIGE® V+VEE vaccine (available from Intervet Inc, Millsboro, Del.; i.e., Eastern encephalomyelitis (EE) virus, Western encephalomyelitis (WE) virus, Venezuelan encephalomyelitis (VE) virus, equine herpes virus type 1 (EHV-1), equine herpes virus type 4 (EHV-4), equine influenza virus (EIV) strain Kentucky 1993/A2, EIV strain Kentucky 2002/A2, and EIV strain New Market/2/93/A2, and tetanus toxoid fractions). These results established the noninterference of the other vaccine fractions on the Killed Flavivirus Chimera fraction.

While the invention has been described in connection with specific embodiments and examples thereof, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements and/or components, it will be understood that the embodiments are capable of different dimensional characteristics and/or measurements and/or components without departing from the principles of the invention and the appended Claims are intended to cover such differences. Furthermore, all patents, printed publications, and the like mentioned herein are hereby incorporated by reference.

What is claimed is:

1. An equine vaccine comprising an immunogenically protective amount of an inactivated chimeric flavivirus for protecting equine animals against West Nile virus infection, wherein said inactivated chimeric flavivirus consists essentially of a yellow fever virus in which the nucleotide sequences encoding the pre-membrane and envelope proteins have been replaced with nucleotide sequences encoding pre-membrane and envelope proteins of a West Nile virus.

2. The vaccine of claim 1, wherein the yellow fever virus is from the 17D strain.

3. The vaccine of claim 1, wherein the chimeric virus comprises a signal sequence at the amino acid terminus of the pre-membrane protein, and the signal sequence is that of yellow fever virus.

4. The vaccine of claim 1, wherein the inactivated chimeric virus is present in a concentration of from $10^2$ to $10^8$ plaque-forming units (pfu).

5. A method of treating a West Nile Virus infection in an equine animal, the method comprising administering to the animal a vaccine according to claim 1.

6. The method of claim 5, wherein the chimeric flavivirus in the vaccine is administered at a dose ranging between $10^2$ and $10^8$ plaque-forming units (pfu).

7. The method of claim 6, wherein the chimeric flavivirus in the vaccine is administered at a dose ranging between $10^6$ and $10^7$ pfu.

8. The method of claim 5, wherein the inactivated chimeric flavivirus vaccine is administered by a subcutaneous, intramuscular, submucosal, mucosal, or intradermal route.

9. The method of claim 5, wherein the inactivated chimeric flavivirus vaccine is orally administered.

* * * * *

UNITED STATES PATENT AND TRADEMARK OFFICE
CERTIFICATE OF CORRECTION

| | | |
|---|---|---|
| PATENT NO. | : 8,048,429 B2 | Page 1 of 1 |
| APPLICATION NO. | : 11/473600 | |
| DATED | : November 1, 2011 | |
| INVENTOR(S) | : Sterner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this
Twenty-first Day of February, 2012

David J. Kappos
*Director of the United States Patent and Trademark Office*